United States Patent
Tsai et al.

(10) Patent No.: US 10,556,054 B1
(45) Date of Patent: Feb. 11, 2020

(54) BLOOD LEAKAGE WARNING DEVICE FOR DIALYSIS PATIENT

(71) Applicants: Wei-Te Tsai, Kaohsiung (TW);
Kee-Chong Yu, Kaohsiung (TW)

(72) Inventors: Wei-Te Tsai, Kaohsiung (TW);
Kee-Chong Yu, Kaohsiung (TW)

( * ) Notice: Subject to any disclaimer, the term of this patent is extended or adjusted under 35 U.S.C. 154(b) by 0 days.

(21) Appl. No.: 16/165,406

(22) Filed: Oct. 19, 2018

(51) Int. Cl.
*A61M 1/36* (2006.01)

(52) U.S. Cl.
CPC ... *A61M 1/3656* (2014.02); *A61M 2205/0233* (2013.01); *A61M 2205/13* (2013.01); *A61M 2205/15* (2013.01); *A61M 2205/18* (2013.01); *A61M 2205/3584* (2013.01); *A61M 2205/581* (2013.01); *A61M 2205/584* (2013.01); *A61M 2205/587* (2013.01)

(58) Field of Classification Search
CPC .......... A61M 1/3656; A61M 2205/587; A61M 2205/13; A61M 2205/3584; A61M 2205/581; A61M 2205/0233; A61M 2205/18; A61M 2205/15; A61M 2205/584
USPC .................................................. 340/539.12
See application file for complete search history.

(56) References Cited

U.S. PATENT DOCUMENTS

| | | | | |
|---|---|---|---|---|
| 4,083,777 | A * | 4/1978 | Hutchisson | A61M 1/16 210/186 |
| 8,398,575 | B1 * | 3/2013 | McCall | A61M 1/3653 600/371 |
| 2008/0041792 | A1 * | 2/2008 | Crnkovich | A61F 13/42 210/739 |
| 2010/0271212 | A1 * | 10/2010 | Page | A61B 5/4216 340/573.1 |
| 2017/0141601 | A1 * | 5/2017 | Halliburton | A61M 1/14 |
| 2017/0326282 | A1 * | 11/2017 | Wilt | A61M 1/1086 |
| 2018/0001021 | A1 * | 1/2018 | Wu | A61M 1/3656 |
| 2018/0064871 | A1 * | 3/2018 | James | A61M 5/16836 |
| 2018/0289885 | A1 * | 10/2018 | Weaver | A61M 1/3656 |

* cited by examiner

*Primary Examiner* — Hirdepal Singh
(74) *Attorney, Agent, or Firm* — Bacon & Thomas, PLLC

(57) ABSTRACT

A blood leakage warning device for dialysis patient is applied to cover an injection site, comprising a cover absorber, two detection modules, a control module and an alarm module. The cover absorber is used for absorbing blood leakage. The two detection modules are disposed on the cover absorber at intervals. The control module is electrically connected to the two detection modules to detect whether the cover absorber absorbs the blood. The alarm module is electrically connected to the control module. The alarm module issues an alarm when the cover absorber absorbs the blood.

9 Claims, 6 Drawing Sheets

US 10,556,054 B1

BLOOD LEAKAGE WARNING DEVICE FOR DIALYSIS PATIENT

BACKGROUND OF THE INVENTION

1. Field of the Invention

The present invention relates to a blood leakage warning device for dialysis patient, particularly used for detecting the blood leakage at the injection site.

2. Description of the Prior Art

The kidney is an organ in vertebrates that is part of the urinary system. They can filter impurities in the blood, maintaining the body fluid balance and the concentration of electrolytes to produce urine to pass outside the body through subsequent ducts. Meanwhile, the kidney also maintains endocrine function to regulate blood pressure.

Physiologically, the kidney can affect the blood flow, blood composition, blood pressure, bone development, and takes part in important metabolic function. Therefore, if relative diseases occur, it will cause dysplasia, edema or dehydration, and immune system disorder. Moreover, it can even lead to death.

Renal failure means kidney diseases which result from kidney failure, and it can't effectively remove impurities in the blood, so that the metabolic function is affected. In severe cases, it can be fatal.

The two main causes of renal failure are acute kidney injury and chronic kidney disease. Acute kidney injury can be cured under proper treatment, but chronic kidney disease is usually irreversible reduction in renal function.

When the impurities in the blood cannot be removed due to renal disease, dialysis is used to remove the impurities in the blood. The common treatments include hemodialysis and peritoneal dialysis.

Hemodialysis is a treatment that uses a hemodialysis machine to extract blood from the patients' body to outside, filtering the waste and excess water in the blood, and send clean blood back to body. In general, the patients need to go to hospital or professional hemodialysis center, and the hemodialysis should be performed by the medical staff, so the time schedule is less flexible. The hemodialysis treatment should be performed three times a week to maintain the condition of the patient's blood.

Peritoneal dialysis does not extract the blood, but instead uses the patients' peritoneum as a medium to inject dialysate to absorb excess water and waste in the body and pass them outside the body. Peritoneal dialysis can be performed by patients or caregiver at home or in a place suitable for dialysis after being instructed by the medical staff. Using peritoneal dialysis to remove impurities from the blood must be performed three times a day to maintain the condition of the patient's blood. Compared with hemodialysis, the time schedule of peritoneal dialysis is more flexible, and it does not damage the patient's residual renal function.

Both hemodialysis and peritoneal dialysis have to enter the patient's body with a pinhole or fistula. Therefore, there is a risk of blood leakage occurring during dialysis, which means the patient's blood will leak from the pinhole or outside of the fistula, or a large amount of blood emanating from the wound resulting from extravasation. If the patient is taking anticoagulant drugs, it may cause a lot of blood loss due to the inability of the wound to coagulate. Especially, because peritoneal dialysis can be performed at home, if massive blood loss occurs, there is no medical staff to monitor the patient's safety. Moreover, both hemodialysis and peritoneal dialysis extract the blood from the patient's body to the dialysis machine for filtration, and then drain the blood back to the body. If there is extravasation or blood leakage occurring in the process, and the nurse does not notice it in the first place, it will lead the patient in a coma caused by a large number of blood leakage, and eventually it will cause loss of life.

The bleeding from the needle-stick site is unavoidable, but if the bleeding does not stop which is dangerous to life. Referring to FIG. 1, it is Taiwan Patent No. 1569845, a needle dislodgment and blood leakage detection device, comprising a sensing component 11 provided with a flexible sensor, and a warning device 12 provided for the sensing component 11. The sensing component 11 is provided with two blood leakage sensing electrodes surrounding the needle-stick site in the patient's arm. The two blood leakage sensing electrodes will be short-circuited by a needle, or by the blood leaking from the needle-stick site. The warning device 12 like a wristwatch can be worn on the wrist of the patient, which can be electrically connected to the two blood leakage sensing electrodes, and sends out a warning message when the two blood leakage sensing electrodes are short-circuited.

From the above descriptions, although the prior art device discloses a warning device for needle dislodgment and blood leakage detection to avoid continuous blood loss, but the following disadvantages are still in the actual usage:

1. Complicated procedures difficult to perform

The flexible sensor must be attached to the patient's injection site before the needle insertion procedure. Firstly, the warning device needs to be attached to the wrist of the patient. Then, the warning device is electrically connected to the flexible sensor. Lastly, the needle insertion can be performed. For the medical staff, the procedures are complicated and difficult to perform.

2. Connection between the warning device and the flexible sensor easy to fall off In the prior art device, the warning device disposed on the wrist is connected to the flexible sensor in a straight line. Since the length of the flexible sensor is fixed, the required distance must be determined in advance to set the flexible sensor. The flexible sensor uses tab-shaped end insertion, which is easily separated from the warning device due to patient's wrist movement and restoring force of the flexible sensor, thereby losing the warning function.

3. Unable to dispose on other parts of the body

The prior art blood leakage detecting device can only be applied to the arm, and is not suitable for other parts, not to mention the peritoneal dialysis. Therefore, the application is limited.

Therefore, how to precisely detect the blood leakage and provided to the dialysis patients, and let the patient and the medical staff detect the blood leakage at the first place, and at the same time convenient to the medical staff to operate, is the objection eagerly to be achieved by the relative technical staff.

SUMMARY OF THE INVENTION

Therefore, an objective of an embodiment of the present invention is to provide a blood leakage warning device for dialysis patient applied to cover an injection site, comprising a cover absorber, two detection modules, a control module and an alarm module.

The cover absorber is used for absorbing blood leakage.

The two detection modules are disposed on the cover absorber at intervals.

The control module is electrically connected to the two detection modules to detect whether the cover absorber absorbs the blood.

The alarm module is electrically connected to the control module. The alarm module issues an alarm when the cover absorber absorbs the blood.

Another technique of an embodiment of the present invention is that the present invention further comprises two assemblies which are respectively disposed between the two detection modules and the control module, so that the two detection modules and the control module are detachable for assembly.

Another technique of an embodiment of the present invention is that the two detection modules respectively include plural conductive fibers, and the plural conductive fibers are disposed at intervals.

Another technique of an embodiment of the present invention is that the control module includes a power supply unit, and the power supply unit provides power for the present invention.

Another technique of an embodiment of the present invention is that the control module includes a switch unit and a function light, the switch unit used for controlling the operation of the present invention, and the function light displays the function status of the present invention.

Another technique of an embodiment of the present invention is that the alarm module includes an alarm signal light and a sound transmitter, the control module controls the frequency of the sound transmitter based upon the amount of the blood leakage.

Another technique of an embodiment of the present invention is that the present invention comprises a transmission module, the transmission module can transmit data to a portable device, and the control module includes a memory unit, the memory unit can store the basic information of person relative to the injection site.

Another technique of an embodiment of the present invention is that the cover absorber is further provided with at least a fixing tape to fix the cover absorber on the dialysis patients' body.

An advantage of an embodiment of the invention is that the cover absorber is made from textile material, and when the cover absorber covers the injection site and blood leakage occurs at the injection site, the cover absorber will absorb the blood; when the cover absorber absorbs the blood, it will alter the resistance between the two detection modules, and the control module detects the difference of resistance to identify the blood leakage; when the patient has blood leakage, the control module enables the alarm module to issue an alarm.

DETAILED DESCRIPTION OF THE PREFERRED EMBODIMENTS

Specific structural and functional details disclosed herein will become apparent from the following description of three preferred embodiment of the present invention taken in conjunction with the accompanying drawings, which provides better understanding to a person having ordinary skill in the art but shall not be construed as limiting the invention. Before explaining the present invention in detail, it is to be understood that similar elements are labeled with the same number.

Figure 1:
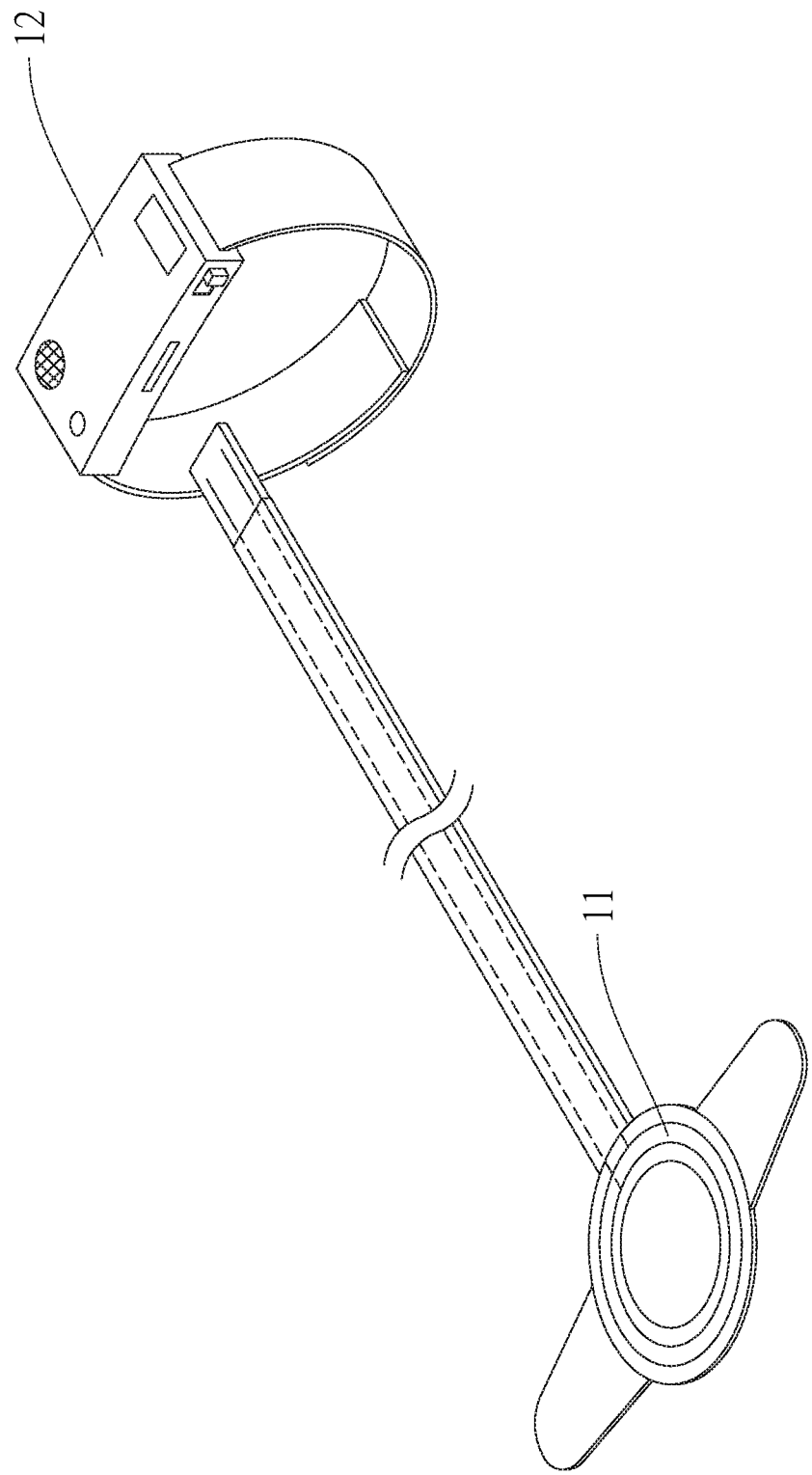
FIG. 1 is a drawing of Taiwan Patent No. 1569845, a needle dislodgment and blood leakage detection device.
Figure 2:
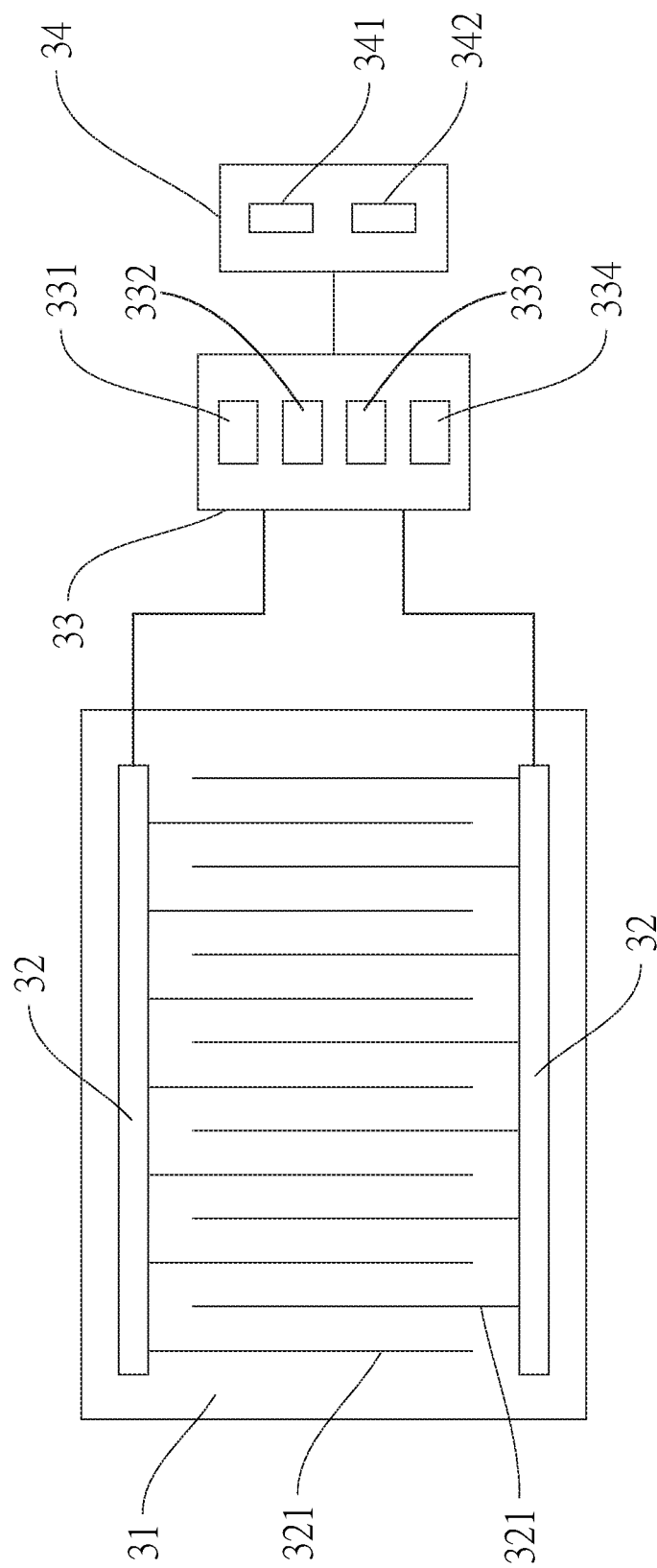
FIG. 2 is a drawing of a first preferred embodiment according to the present invention.
Figure 3:
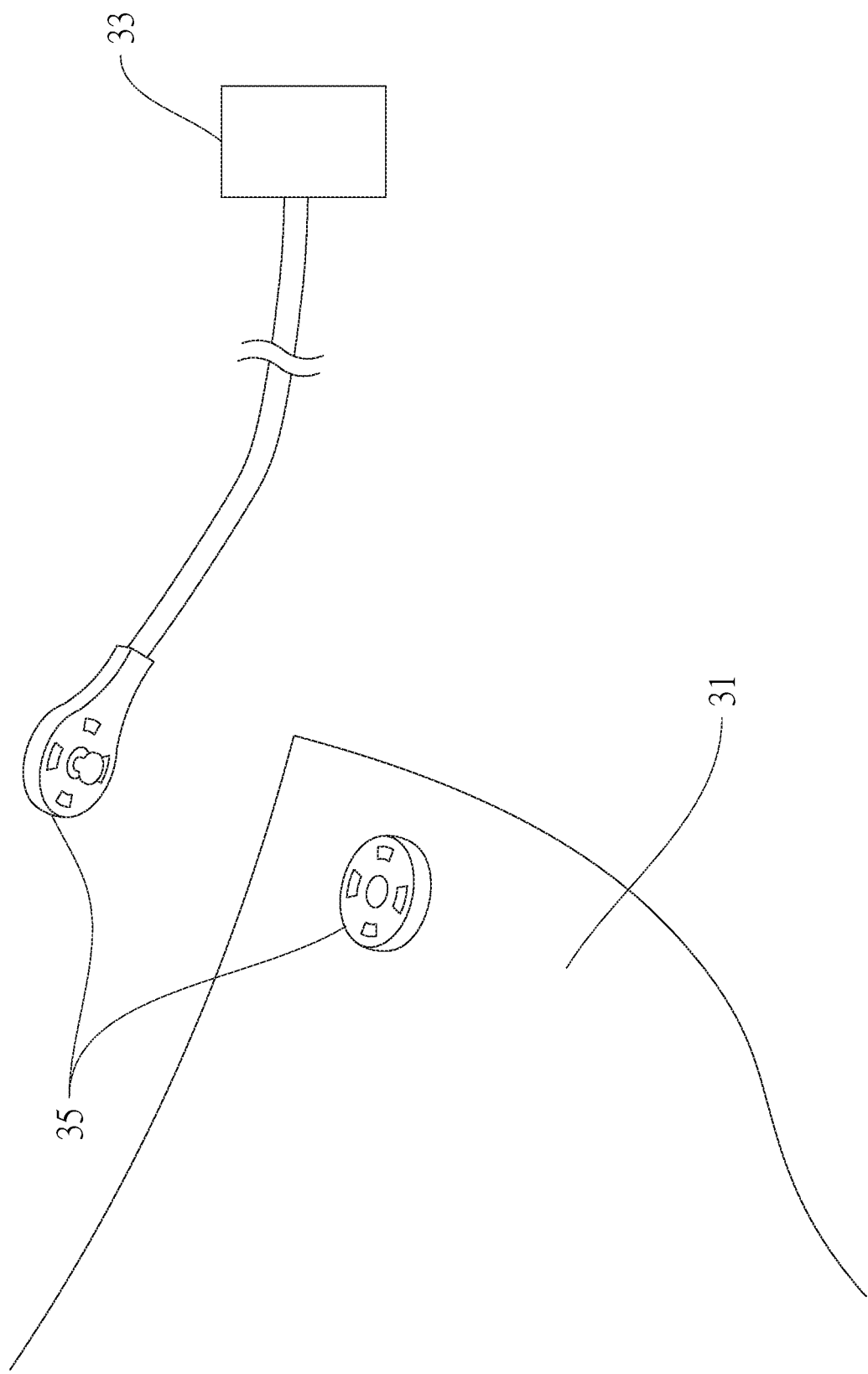
FIG. 3 is a drawing of an assembly of the first preferred embodiment.
Figure 4:
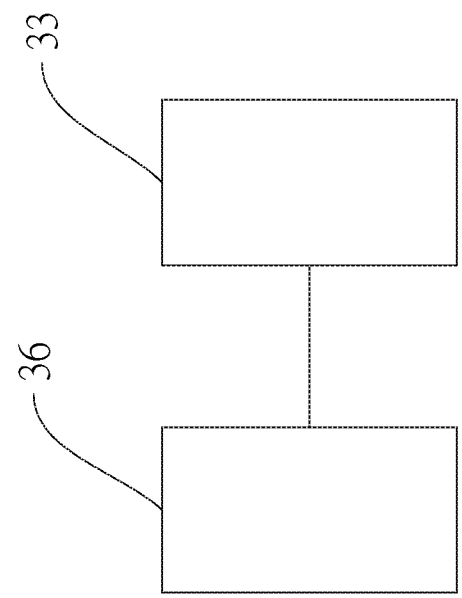
FIG. 4 is a drawing of a transmission module of the first preferred embodiment.
Figure 4:
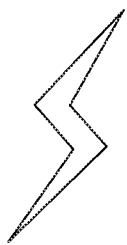
Figure 4:
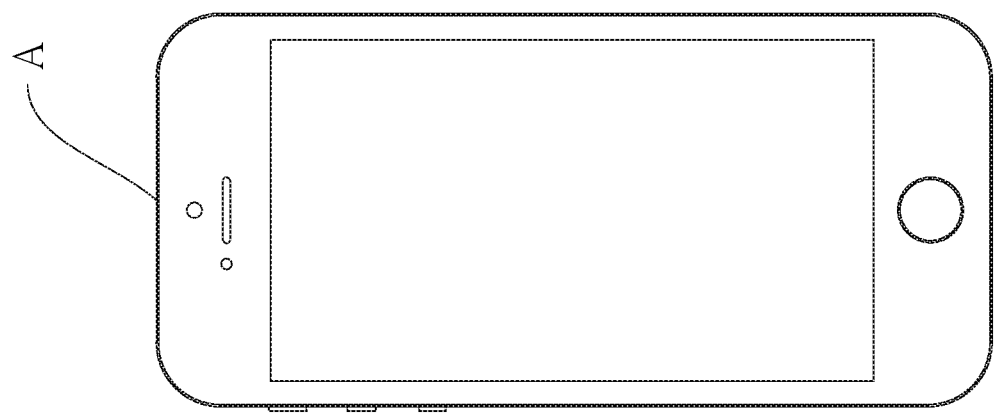

With reference to FIGS. 2,3 and 4, a first preferred embodiment according to the present invention is depicted, which is used for identifying the blood leakage occurring at an injection site (not shown in Fig.). The injection site can be anywhere on the body, for example, the injection site where the medical needle enters could be on the blood vessels of arm, the blood vessels of neck, the lung, the abdominal cavity (peritoneal) insertion, the blood vessel of the thigh.

The present invention comprises a cover absorber 31, two detection modules 32, a control module 33, an alarm module 34, two assemblies 35, and a transmission module 36.

The cover absorber 31 is made from textile material. The cover absorber 31 covers the injection site. When the needle is perfectly inserted into the injection site, the cover absorber 31 will not absorb the blood, but shield the injection site. When the needle is not perfectly inserted into the injection site, the blood or body fluid will flow out from the outside of the needle, and the cover absorber 31 can absorb the leaked blood or body fluid.

The two detection modules 32 are disposed on the cover absorber 31 at intervals. The two detection modules 32 are two metal plate disposed on the cover absorber 31. Preferably, the two detection modules 32 are disposed on the two ends of the cover absorbers 31. The two detection modules 32 respectively include plural conductive fibers 321, and the plural conductive fibers 321 are disposed at intervals. The technique of conductive fibers is a common prior art, not a primary feature of the present invention, and so relative details are not explained further herein. In implementation, the plural conductive fibers 321 are not required, and shall not be construed as limiting the invention.

The control module 33 is electrically connected to the two detection modules 32 to identify whether the cover absorber 31 absorbs the blood. The control module 33 is connected to the two detection modules 32 by two wires respectively to obtain the resistance value between the two detection modules 32, and further to identify whether the cover absorber 31 absorbs the blood. When the cover absorber 31 does not absorb the blood, the resistance value between the two detection modules represents open circuit; when the cover absorber 31 absorbs the blood, the resistance value between the two detection modules represents short circuit. The technique of blood detection is a common prior art, which is widely used for detecting blood sugar, and so relative details are not explained further herein. In implementation, the control module 33 should set different parameters like conductivity, resistance of short circuit/open circuit based upon conditions like size of the cover absorber 31, thickness of the cloth.

The control module 33 includes a power supply unit 331, a switch unit 332, a function light 333 and a memory unit 334.

The power supply unit 331 provides power for the present invention. The power supply unit 331 can be a battery to provide direct current for the electronic components. The power supply unit 331 also can be a transformer to convert alternating current for the electronic components.

The switch unit 332 used for controlling the operation of the present invention. When the cover absorber 31 is electrically connected to the control module 32, and the cover absorber 31 covers the injection site, and turns on the present invention via the switch unit 332 to identify the leaked blood. When the leaked blood detection is not required, the present invention can be turned off via the switch unit 332. When the present invention is turned on, the function light 333 will show green light to indicate that the present invention starts to identify the leaked blood. When the present invention is turned off, the function light 333 goes out.

The memory unit 334 can store the basic information of personnel contacting the injection site, such as medical staff, patients and patient's family. In the first preferred embodiment, the memory unit 334 stores the patient's emergency contact information (like medical staff or family). When the control module 33 identifies the blood leakage, it can send notification to the emergency contact's portable device A via the transmission module, so that it can prevent the user (the dialysis patient) from being in a coma caused by massive blood loss without any first aider. Besides, the memory unit 334 can record the patient's injection time to provide to the patient or medical staff.

The alarm module 34 is electrically connected to the control module 33. The alarm module 34 controlled by the control module 33 issues an alarm when the control module 33 detects that the cover absorber 31 absorbs the blood. Preferably, the alarm module 34 includes an alarm signal light 341 and a sound transmitter 342. The alarm signal light 341 will emit a light alarm, and the sound transmitter 342 will emit an audible alarm. When the control module 33 identifies the person has a large amount of bleeding, the alarm signal light 341 is controlled to emit a red light, and the sound transmitter 342 is further controlled to emit an audible alarm to remind the medical staff near the patient to help.

The control module 33 controls the frequency of the sound transmitter 342 based upon the amount of the blood leakage. For example, if the amount of the blood leakage is increasing, the more urgent the audible alarm is emitted, or the blinking frequency of the alarm signal light 341 is controlled to become faster.

In the first preferred embodiment, the two assemblies 35 are made from metal, and the two assemblies 35 are push buttons. The two assemblies 35 are respectively disposed between the two detection modules 32 and the control module 33, so that the wire of the two detection modules 32 and the control module 33 are detachable for assembly, and the cover absorber 31 can be cleaned and sterilized for reuse. In implementation, the two assemblies 35 can be made from other conductive materials, and shall not be construed as limiting the invention.

In the first preferred embodiment, the transmission module 36 is a WiFi wireless transmission module, which can be connected to a WiFi access point, and transmits the data stored in the memory unit 334 to a portable device A via network communication technology, so that the patient's emergency contact can instantly receive the blood leak notification of the patient.

Figure 5:
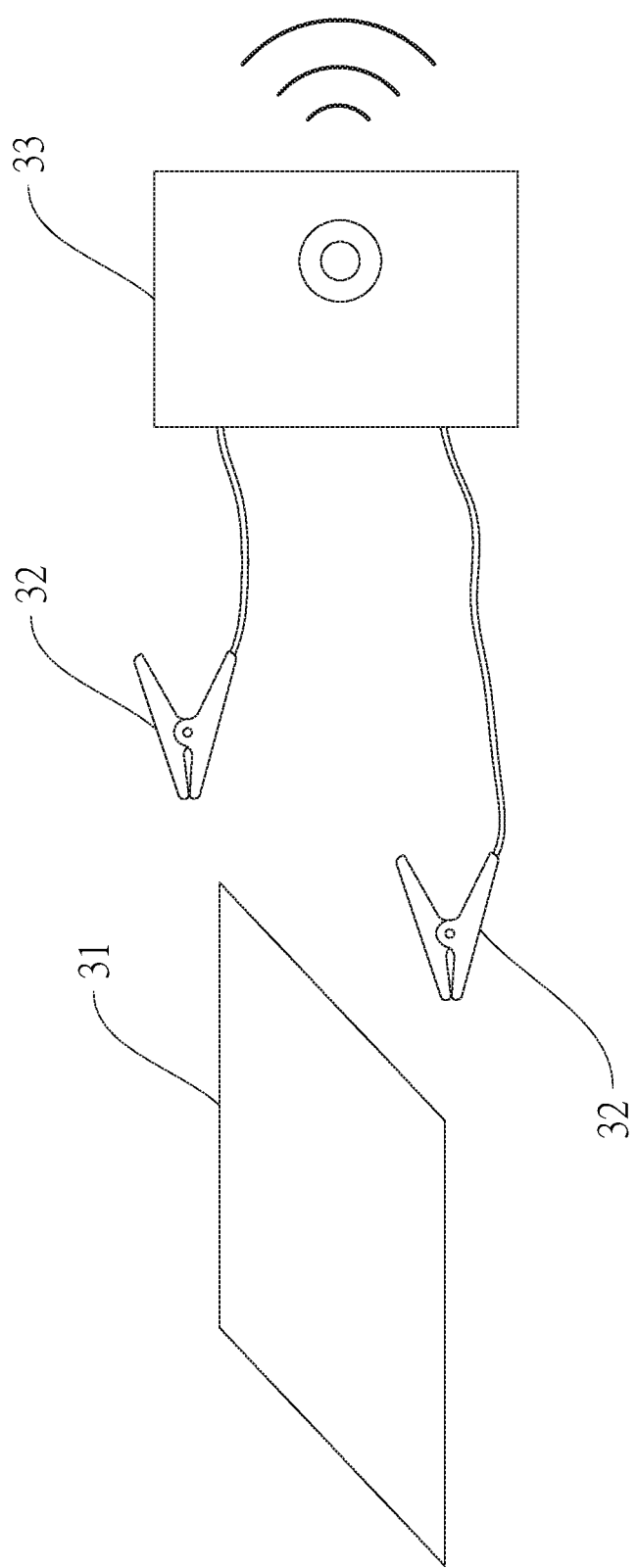
FIG. 5 is a drawing of a second preferred embodiment according to the present invention.

Referring to FIG. 5, a second preferred embodiment according to the present invention is depicted which is similar to the first embodiment, and so common features are not described again. The difference is that the cover absorber 31 is made from disposable textile material (such as non-woven fabric) and composed of fibers with good moisture absorption. The cover absorber 31 is generally opaque to cover and shield the needle insertion of the injection site, and further it absorbs blood leakage when the needle insertion leaks blood.

The cover absorber 31 is not provided with any conductive material, and is a disposable product. Dialysis patients should replace the needle after each use to avoid infection, no matter the injected pinhole has blood leakage or not. Preferably, the cover absorber 31 can select an appropriate size of gauze (or non-woven fabric). In implementation, other fibrous materials can be used, and shall not be construed as limiting the invention.

In the second preferred embodiment, the two detection modules 32 are metal clamps for clamping the two sides of the cover absorber 31. The control module 33 can detect the resistance change of the cover absorber 31, and further enable the control module 33 to identify the blood leakage if occurring at the injection site of the dialysis patient.

Figure 6:
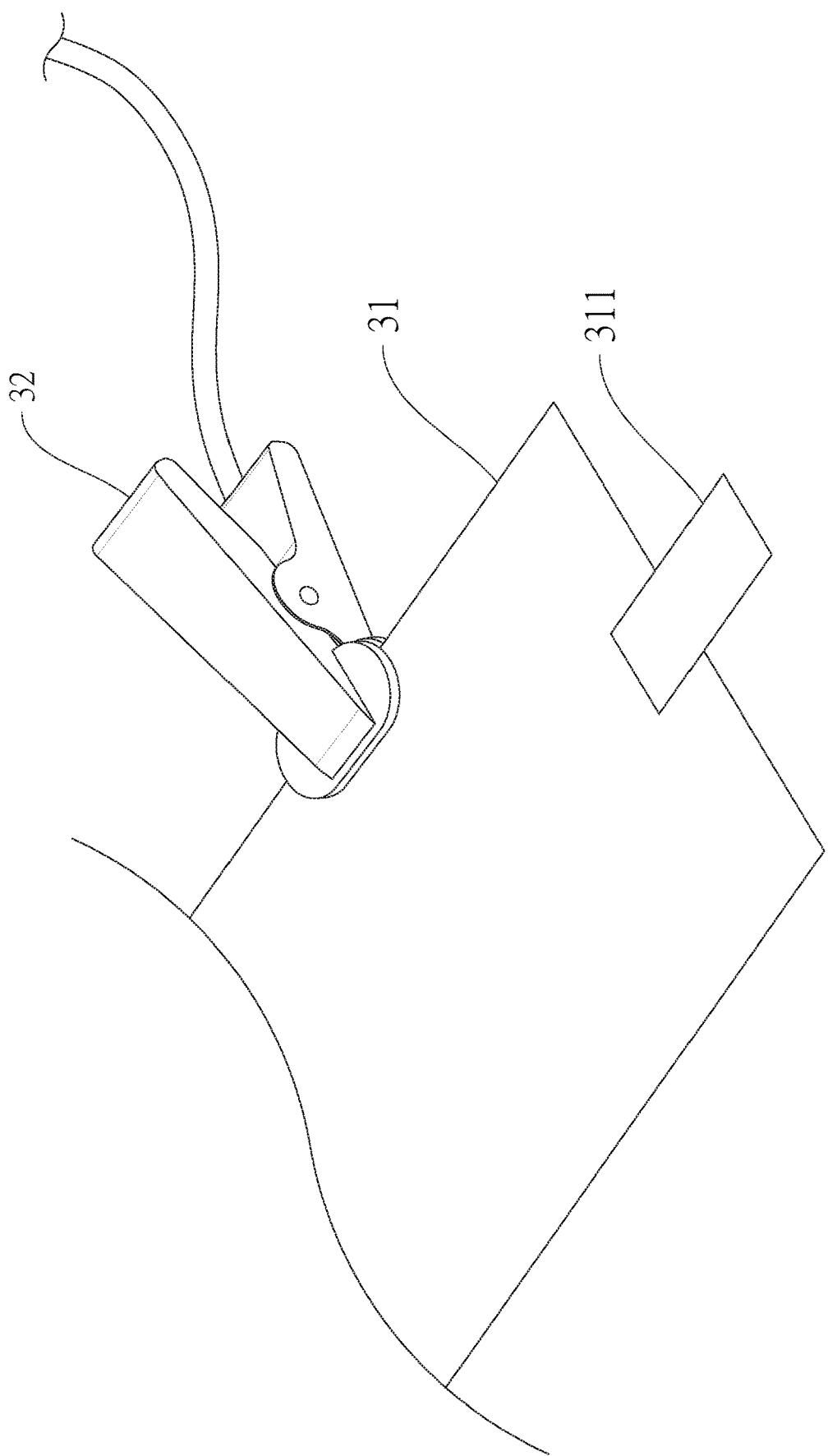
FIG. 6 is a drawing of a third preferred embodiment according to the present invention.

Referring to FIG. 6, a third preferred embodiment according to the present invention is depicted which is similar to the second embodiment, and so common features are not described again. The difference is that the front end of the two detection modules 32 is a large flat surface, and the cover absorber 31 is further provided with at least one fixing tape 311 to fix the cover absorber 31 on the dialysis patient's body, so the cover absorber 31 will not fall off due to wind blowing or body movement. By the large flat front end of the two detecting modules 32, the sensing electrode can be mounted on the surface, and more precise detection of blood leakage can be obtained.

The two detection modules 32 can clamp the two sides of the cover absorber 31, and when the large flat metal front end of the two detection modules 32 clamps the cover absorber 31, it can be more precisely detect the resistance change of the cover absorber 31, and further enables the control module 33 to identify the blood leakage if occurring at the injection site of the dialysis patient.

With the above descriptions, following advantages can be obtained by the present invention:

1. To prevent from massive blood leakage
   The control module can detect whether the cover absorber absorbs the blood or not, and issues an alarm when the cover absorber absorbs the blood, so that the user can be helped in first place to prevent from massive blood leakage.
2. Issuing an alarm via internet
   The transmission module can help the control module to notify the portable device, and issue an alarm via internet, so that it can prevent the patient from being in a coma caused by blood leakage.
3. Easy to clean or to replace
   The assemblies can separate the cover absorber and the wires for cleaning and sterilization, and the cover absorber can be reused and is easy to replace.

In conclusion, the cover absorber of the present invention can shield the patient's injection site to have an aesthetic effect. When the blood leakage occurs at the injection site, the cover absorber can absorb the leaked blood, and the control module can detect whether the cover absorber absorbs the blood or not. When the cover absorber absorbs the blood, the control module controls the alarm module to emit an audible and light alarm, and further controls the transmission module to notify the patient's emergency contact to prevent the patient from being in a coma caused by massive blood loss without any first aider.

The foregoing embodiment is merely in relation to three preferred embodiments and shall not be construed as limiting the invention. It is to be understood that many other possible modifications and variations can be made without departing from the spirit and scope of the invention as hereinafter claimed. The scope of the present invention shall be construed by claims.

What is claimed is:

1. A blood leakage warning device for dialysis patient used for identifying the blood leakage at an injection site, comprises:
   a cover absorber, covering the injection site used for absorbing blood leakage;
   two detection modules, being disposed on the cover absorber at intervals;
   a control module, being electrically connected to the two detection modules for detecting whether the cover absorber absorbs the blood; and
   an alarm module, being electrically connected the control module, and the alarm module issuing an alarm when the cover absorber absorbs the blood;
   wherein the cover absorber is made from fibrous materials, each of the two detection modules is a clamp, and the two detection modules clamp the cover absorber; and
   wherein when the cover absorber does not absorb the blood, a resistance value between the two detection modules represents an open circuit, and when the cover absorber module absorbs the blood, a resistance value between the two detection modules represents a short circuit.

2. The blood leakage warning device for dialysis patient as claimed in claim 1, wherein the contact surface where each detection module is connected to the cover absorber is approximately close to a plain surface.

3. The blood leakage warning device for dialysis patient as claimed in claim 1, further comprises two assemblies which are respectively disposed between the two detection modules and the control module, so that the two detection modules and the control module are detachable for assembly.

4. The blood leakage warning device for dialysis patient as claimed in claim 1, wherein the two detection modules respectively include plural conductive fibers, and the plural conductive fibers are disposed at intervals.

5. The blood leakage warning device for dialysis patient as claimed in claim 1, wherein the control module includes a power supply unit, and the power supply unit provides power for the blood leakage warning device.

6. The blood leakage warning device for dialysis patient as claimed in claim 1, wherein the control module includes a switch unit and a function light, the switch unit used for controlling the operation of the present invention, and the function light displays the function status of the blood leakage warning device.

7. The blood leakage warning device for dialysis patient as claimed in claim 1, wherein the alarm module includes an alarm signal light and a sound transmitter, and the control module controls the frequency of the sound transmitter based upon the amount of the blood leakage.

8. The blood leakage warning device for dialysis patient as claimed in claim 1, further comprises a transmission module configured to transmit data to a portable device, and the control module includes a memory unit configured to store the basic information of the operator and patients.

9. The blood leakage warning device for dialysis patient as claimed in claim 1, wherein the cover absorber is further provided with at least a fixing tape to fix the cover absorber on the dialysis patients' body.

\* \* \* \* \*